(12) United States Patent
Andreiko

(10) Patent No.: US 6,358,044 B1
(45) Date of Patent: *Mar. 19, 2002

(54) VISUAL POSITIONING ORTHODONTIC APPLIANCE AND METHOD

(75) Inventor: Craig A. Andreiko, Alta Loma, CA (US)

(73) Assignee: Ormco Corporation, Orange, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/422,495

(22) Filed: Oct. 21, 1999

Related U.S. Application Data (63) Continuation of application No. 08/933,269, filed on Sep. 18, 1997, now Pat. No. 5,993,206, which is a continuation of application No. 08/641,903, filed on May 2, 1996, now abandoned.

(51) Int. Cl.[7] .................................................. A61C 3/00
(52) U.S. Cl. ........................................................... 433/9
(58) Field of Search ............................. 433/8, 9, 10, 16, 433/17, 24

(56) References Cited

U.S. PATENT DOCUMENTS

| | | |
|---|---|---|
| 3,345,745 A | 10/1967 | Muller |
| 3,936,939 A | 2/1976 | Faunce |
| 4,386,908 A | 6/1983 | Kurz |
| D302,588 S | 8/1989 | Jones |
| 5,022,854 A | 6/1991 | Broughton et al. |
| 5,542,844 A | 8/1996 | Perret, Jr. |
| 5,993,205 A | 11/1999 | Heiser et al. |
| 5,993,206 A | * 11/1999 | Andreiko ........................ 433/9 |

* cited by examiner

*Primary Examiner*—Ralph A. Lewis
(74) *Attorney, Agent, or Firm*—Wood, Herron & Evans, L.L.P.

(57) ABSTRACT

Orthodontic appliances such as orthodontic brackets are provided with bases that are shaped to correspond to the profiles of the specific teeth to which they are to be attached. The shapes of the bases facilitate the visual placement of the appliances on the teeth of patients by visually signaling to the practitioner the positioning of the appliance with the base thereof centered on the facial side of the tooth. This invention further facilitates the positioning of an archwire support of the appliance at a position on a tooth that is offset from the facial axis or from the center of the face of the tooth by manufacture of the appliance with the support offset from the center of the tooth-shaped pad. Preferably, the appliance base is a scaled reduction of the profile of the tooth, viewed from its facial side. The base is preferably scaled differently in the vertical and horizontal directions, with the shape of the base being reduced from that of the tooth profile by a greater amount vertically than horizontally. The tooth-shaped bases further facilitate identification of the specific tooth for which the appliance is intended.

20 Claims, 4 Drawing Sheets

VISUAL POSITIONING ORTHODONTIC APPLIANCE AND METHOD

This application is a continuation application of U.S. Ser. No. 08/933,269, filed Sep. 18, 1997 now U.S. Pat. No. 5,993,206; which is a continuation application of abandoned U.S. application Ser. No. 08/641,903, filed May 2, 1996, both entitled "Visual Positioning Orthodontic Appliance and Method", hereby expressly incorporated by reference herein.

FIELD OF THE INVENTION

This invention relates to the positioning of orthodontic appliances on the teeth of a patient, and more particularly, to the configuration of orthodontic appliances, particularly orthodontic brackets, for the visual positioning thereof on the teeth of patients.

BACKGROUND OF THE INVENTION

When bonding orthodontic appliances, a major tenet to be considered by the orthodontist is the location of the appliance in the mouth of the patient. In the case of bonded orthodontic brackets, this location is the position and orientation of each of the brackets on one of the teeth of the patient.

Figure 1A:
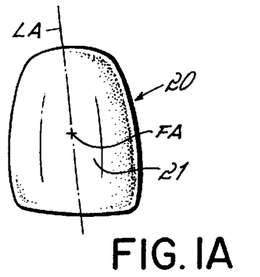
FIGS. 1A through 1H are a series of diagrams illustrating problems in the visual placement of orthodontic appliances on teeth with appliances of the prior art.
Figure 1B:
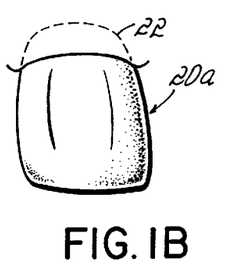
Figure 1C:
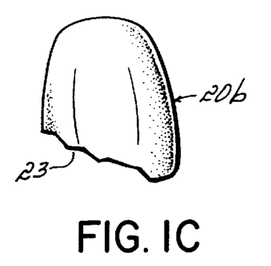

Most of the preadjusted appliances that are currently employed for maxillary application are designed to be located at the facial axes of the maxillary teeth of the patient. The facial axis, or FA point of a tooth illustrated as Point FA in FIG. 1A, is defined as dead center vertically on the clinical facial surface of a fully erupted crown and at the height of contour mesiodistally of the mid-developmental lobe of the tooth, for example, right maxillary central 20. This definition is based on the criteria that the plane of the archwire will pass through the point FA. Furthermore, appliances should be aligned angularly in the FA plane, which is the plane tangent to surface of the tooth at the FA point, at a line angle represented by line LA in FIG. 1A. This angle LA generally coincides with the line along the height of the contour of the tooth's mid-developmental lobe 21. So angularly aligned, the appliance will better deliver the appropriate final angular position or tip of the tooth. These criteria are referred to as the concept of morphological centering and angular alignment. This concept is quite often implemented visually by the orthodontist or other clinician who places the appliance on the tooth by making a visual determination of the location of the point FA and the orientation of the line LA. The visual implementation of this concept can be rendered difficult for the orthodontist by varying degrees of eruption that leaves an unerupted portion 22 of a tooth 20a, as illustrated in FIG. 1B, by virtue of chipped or worn incisal tooth edges 23 of a tooth 20b, as illustrated in FIG. 1C, or by virtue of the existence of other aberrations of the typical tooth profile. Teeth for mandibular application are also often visually placed in accordance with mandibular placement criteria.

While the concept of morphological centering and angular alignment is familiar to orthodontists, the clinical difficulty of achieving its placement goals is well known. Several approaches have been developed to alleviate this problem but all have drawbacks. The most common approach has been to use measuring instruments to position the appliances at fixed vertical heights. These heights typically represent something akin to the average distance from the incisal edge of a tooth to the FA point of the tooth, and are usually expressed in millimeters. The awkwardness of this approach is that teeth come in various sizes, which precludes placement of the appliance at the proportional center of the tooth in all but the truly average patient. Additionally, due to the highly probably presence of a malocclusion and to the lack of access because of the tooth's position in the mouth (e.g. as with posterior segments or crowding) there is often insufficient space to use these instruments effectively.

Figure 1D:
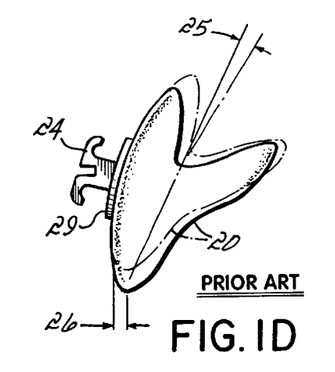

When the appliances are not placed at the design location, adverse effects occur with respect to the final positioning of the teeth. First, if the appliance such as an upper right central bracket 24 is placed incorrectly in the vertical plane, the faciolingual inclination of the tooth is effected, producing an inclination error 25 as illustrated in FIG. 1D. Secondly, at the same time, the apparent thickness of the appliance is effected, resulting in a labial-lingual offset error 26 from the desired placement of a tooth on the dental arch.

Another approach to this problem is that known as "indirect bonding." This approach involves positioning of the appliances on a model or cast of the patient and then using a transfer mechanism or tray to transfer the positioned appliances to corresponding positions on the teeth of the patient. The indirect bonding approach has its detracting features. For instance, often the tray does not seat fully, causing simultaneous incorrect placement of a multitude of individual appliances. Other problems include appliance adhesive failure and excessive "flash." Further, brackets are typically, although not always, placed by eye on the model, which offers little improvement over direct placement on most patients. These difficulties have been sufficient to severely limit the use of the indirect bonding technique.

Figure 1E:
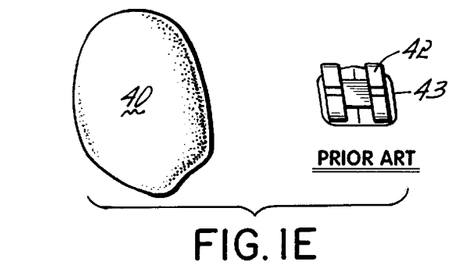
Figure 1F:
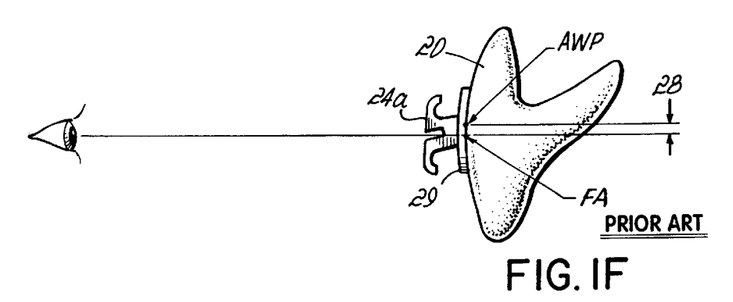

An understanding of why the centering and aligning of appliances has been so clinically troublesome can be obtained by examining the morphology of the appliances and the dentition. Teeth, as most anatomical entities, have a generally flowing shape which does not lend itself to description or visualization using geometric determinants, as can be seen from the profile of a typical upper right cuspid 40 in FIG. 1E. Appliances such as brackets and their bonding pads, on the other hand, are typically generated from orthogonal geometric designs that lend themselves to ease of appliance manufacture, as can be seen from a typical upper right cuspid bracket 42. Further complicating this situation with respect to vertical placement is the varying torque or inclination angle of the archwire slot relative to the base of the appliance. This occurs whether an angle of a slot is cut in a bracket support, i.e. "torque in the face", or an angle is formed in the mounting surface of a bracket, e.g., "torque in the base". Because of this angle, the true plane of the archwire, which should intersect the FA point, is difficult for the orthodontist to visualize. Thus, positioning of the appliance, such as with the illustrated high torque upper right central bracket 24a, using either the bracket body or the facial view of the slot, will yield the positioning of the bracket on a tooth, such as tooth 20, with the archwire plane AWP intersecting the tooth 20 at a point displaced from the point FA, by an amount 28, as illustrated in FIG. 1F. Such a view afforded the clinician when placing the appliances often incorrectly influences the positioning. For the clinician to attempt to minimize this problem by viewing directly into the slot of the appliance during placement is at least awkward and not always possible clinically.

Figure 1G:
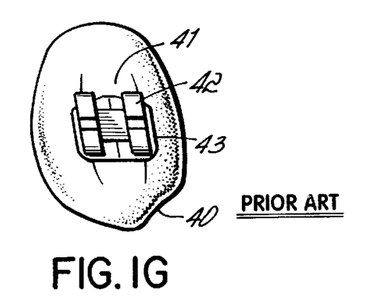
Figure 1H:
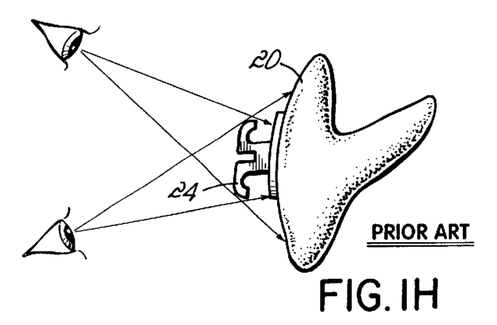

Additionally, when placing the appliance mesiodistally, the geometric appearance of the bracket and bonding pad can also be misleading, as seen when the rhomboid geometry of some individual appliances is compared to the dental anatomy. For example, FIG. 1G illustrates the difference between the shapes of orthogonal upper right cuspid bracket 42 and the anatomical shape of the upper right cuspid 40 with the bracket 42 correctly placed on mid-developmental lobe 41 that is not coincident with the mesiodistal center of the tooth. Further, when a clinician uses the bracket body portion of an appliance as the primary landmark, parallax is also a complicating circumstance that gives the clinician an incorrect apparent view of appliance position, as illustrated in FIG. 1H.

Notwithstanding the problems and disadvantages stated above, the concept of visual positioning of orthodontic appliances on the teeth of patients remains a technique that clinicians must use. Therefore, there remains a need for a solution to the problems of the prior art and for greater accuracy and reliability in visual appliance positioning.

SUMMARY OF THE INVENTION

A primary objective of the present invention is to alleviate the deficiencies of the prior art appliances that render inefficient and imprecise the visual positioning of orthodontic appliances on the teeth of patients. It is a particular objective of the present invention to provide an orthodontic appliance that provides a visual signal to the clinician that enhances the ability and the likelihood of achieving precise and accurate placement of the appliance on the teeth of a patient.

In accordance with the principles of the present invention, the orthodontic appliance, and particularly the portion thereof that lies against the tooth of a patient, is contoured in a way that corresponds to the profile of the tooth on which the appliance is to be positioned, so as to provide a signal that guides the clinician in the easy and precise positioning of the appliance on the tooth. It is a particular objective of the present invention to provide orthodontic appliances with tooth mounting surface thereon that are shaped to provide to the clinician who is placing the appliance on the tooth of a patient a placement signal that will facilitate the centering of the appliance on the tooth of the patient and will override erroneous signals that are caused by irregularities in the actual profile or shape of the patient's teeth.

In accordance with the preferred embodiment of the invention, orthodontic appliances such as orthodontic brackets are provided with bases of pads that have shapes related to the frontal anatomies of the specific respective teeth to which the appliance is to be attached. The archwire support portion of the appliance is, in one embodiment, fixed relative to the pad so that the plane of the archwire passes through the FA point of the tooth when the pad is properly positioned on the tooth. In alternative embodiments, the wire support portion of the bracket is fixed to the pad, extending rigidly from the pad, so that the archwire plane intersects the tooth at a position other than through the FA point that meets some intended placement criteria offset from the FA point.

In one preferred embodiment of the invention, the archwire support portion of a bracket is fixed to a pad so that the pad can be positioned upon the mesiodistal center of the tooth by a visual centering of the tooth in a facial view with the bracket at the height of the contour of the mid-developmental lobe. Such support portions are fixed to the pad, either by being formed separate from the pad and being attached to the pad by welding, fusing or other bonding technique or by being formed integral with the pad in a molding, forging, casting, machining or other such manufacturing operation. The brackets being so formed, the support portion extends rigidly from the pad and is located on the opposite side of the pad from the mounting surface at which the pad is to be attached to a tooth. The position of the archwire support on the pad may be defined in relation to the a point on the mounting surface, thereby making it possible to locate the support by properly positioning the pad on a tooth.

In accordance with the principles of the present invention, the bases or mounting pads of the appliances are shaped to conform to the outlines or profiles of the teeth to which the bases are to attach. The profiles are preferably the silhouettes of the specific teeth when viewed from the facial side of the tooth in a lingual direction in the archwire plane. The sizes of the pads, so shaped, are preferably geometrically reduced or scaled down from the sizes of the profiles of specific teeth. The profile shapes are preferably statistically average shapes for each tooth type among the members of a population segment. The appliances having bases so shaped send to the clinician, who is mounting the appliances on the teeth of a patient, a strong visual signal, which, when received by the eye of the clinician, guides the clinician in the placement of the appliances at the visual centers of the teeth. With the bases or pads to be so located, the archwire support portions of the appliances can be either centered on the bases or offset from the centers of the bases so that they assume their intended positions on the teeth.

With the preferred embodiment of the invention, the shapes of the pads or bases of the appliances are determined by producing an outline or profile of the tooth as would be seen by the installing clinician from the facial side of the teeth. This outline is then scaled downward in size to a size that is appropriate for the appliance base or pad. The size reduction of the shapes from the that of the tooth outline to that of the finished appliance base or pad may be carried out according to a scale that differs in the horizontal and vertical directions. For example, a bracket pad may be scaled in the horizontal direction to 50% of the horizontal dimension of the tooth while being scaled in the vertical direction to 25% of the dimension of the tooth.

The appliances of the present invention and the methods of making and placing such appliances provide the advantages of more efficient and precise visual placement of the appliances on the teeth. In addition, such appliances and methods provide for a reduction in bracket adhesive failure, since the shaped pads may easily have at least a twenty percent increase in bonding area, and in some cases, much more. This increase may be provided without noticeable deterioration in esthetics by carefully enlarging the pad only in areas where the increase would be unnoticed when a ligature and archwire are present. This is accomplished while still maintaining the anatomical placement registration.

In addition, the difficulty of excess adhesive cleanup is reduced because the pads have no sharp corners, so that cleanup can be achieved with fewer discreet moves than with an orthogonal pad. Additionally, the tie wings of the brackets can be more easily made so as not to extend beyond the pad and therefore be less likely to snag on the cleanup instrument and thereby dislodge or alter the position of the appliance. Also, the likelihood of appliance drift prior to adhesive polymerization is further reduced because the ratio of the area of the pad to the mass of the assembly is greater in relation to that of the standard orthogonal pad, thereby lessening the propensity for the appliance to move due to gravity before the adhesive polymerizes.

A further advantage of the tooth-shaped pad is that the pad itself serves as a bracket identifier that is different for each tooth type and also for each quadrant, because the tooth-shaped pads carry tooth specific anatomic information that visually describes which tooth the appliance is designed for, simplifying identification of the particular appliance.

Patient hygiene and iatrogenic decalcification are improved with the tooth-shaped pads because the bracket tie wings need not exceed the perimeter of the pads, and therefore the patient is able to access this area with a toothbrush to minimize the decalcification commonly seen at the gingival edge of the pad. Additionally, the pads may be designed to cover the gingival areas where decalcification is common.

The quality of pad fit with respect to tooth curvatures is further increased with the pads shaped according to the present invention, because, while the pad of a standardized bracket is unlikely to fit any tooth perfectly, the tooth-shaped pads have less in the way of corners than do orthogonal pads, so teetering across the diagonal corners of the orthogonal pads is lessened.

The present invention is particularly advantageous in the application of appliances to the maxillary teeth, although certain features of the invention provide advantages in the application of appliances to mandibular teeth.

These and other objectives and advantages of the present invention will be more readily apparent from the following detailed description of the drawings of the preferred embodiment of the invention, in which:

BRIEF DESCRIPTION OF THE DRAWINGS

FIG. 4A is a facial diagram illustrating the prior art placement of a set of conventional brackets on right maxillary teeth, while

DETAILED DESCRIPTION OF THE DRAWINGS

The present invention recognizes that many errors occurring in the orthodontic positioning of appliances on teeth are caused by erroneous visual signals that result from a lack of similarity between different shapes. With the present invention, the appliance is rendered easy to position by providing the bonding pad to which the appliance is precisely fixed with a shape related to the outline of the tooth to which it is to attach. With the present invention, the bracket is located with sufficient precision on the pad, which results in variations in placement being lessened by the more dominant visual signal sent to the clinician due to the congruity of the pad and the dental anatomy. With the preferred embodiment of the invention, brackets are provided with pads that, for each tooth type, are shaped to conform to the dental anatomical outlines of the specific tooth of the type to which the bracket is to attach, with geometric reductions then performed on the pad shapes for each tooth type to create reduced size shapes that send more "signal" to the eye of the clinician.

Figure 2:
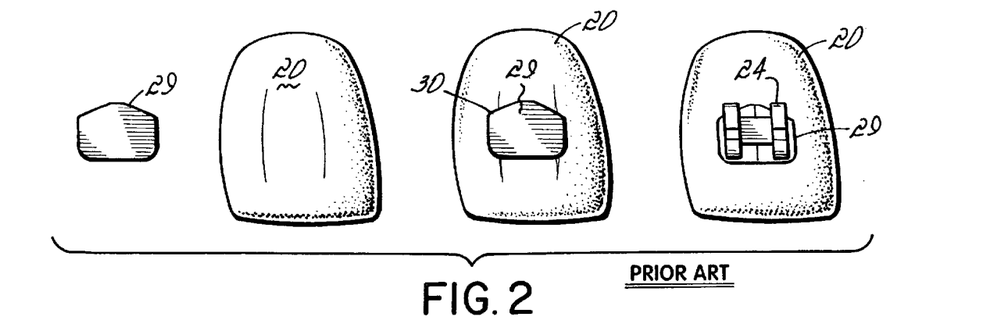
FIG. 2 is a series of diagrams illustrating the prior art placement of a conventional appliance on a tooth.

FIG. 2 illustrates the outline of a pad 29 of a conventional maxillary right central bracket, the outline of the maxillary right central tooth 20, the pad outline 29 properly positioned on the tooth 20, and the assembled conventional bracket 24 with its pad 29 positioned on the tooth 20. The pad 29 of the bracket 24 has a standard orthogonal shape. As can be seen from FIG. 2, when centered on the tooth 20, the upper left corner 30 of the pad 29 is the closest to the perimeter of the profile of the tooth 20, making the pad 29 and bracket 24 appear to be off center to the left. Such a visual signal has a tendency of causing the clinician to place the bracket 24 on the tooth slightly to the clinician's right of its proper position.

Figure 3:
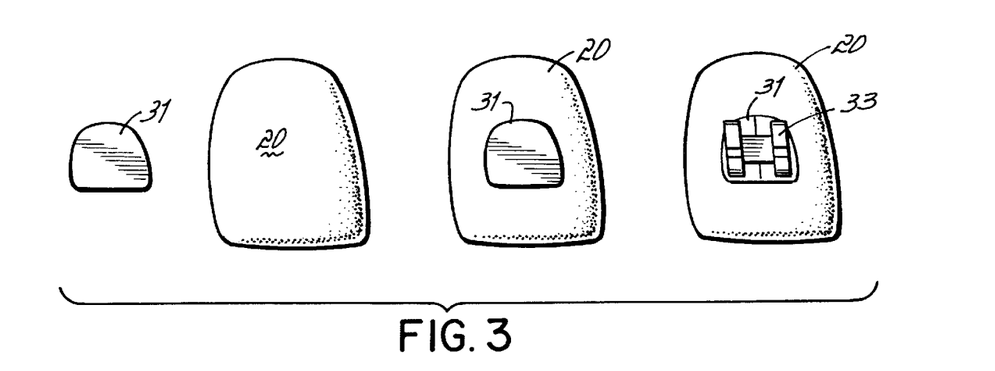
FIG. 3 is a series of diagrams illustrating the placement on a tooth of an appliance embodying principles of the present invention.

Referring to FIG. 3 is illustrated the outline of a pad 31 of a maxillary right central appliance according to principles of the present invention. The pad 31 has the same general peripheral shape as the outline of the maxillary right central tooth 20. When the pad 31 is properly centered on the tooth 20, the outline of the pad 31 is proportionately spaced from the outline of the profile of the tooth 20 and appears visually centered on the tooth 20. Thus, a maxillary right central bracket 33 that is similar to the standard bracket 24 but has the tooth-shaped pad 31 has the visual appearance of being centered on the tooth 20. Such a tooth-shaped pad 31 gives a visual signal to the clinician who is placing the bracket 33 on the tooth 20 that the bracket 33 is properly centered on the tooth 20. With the pad 31 of the bracket 33 so shaped to conform to the outline of a maxillary right central 20, the practitioner receives this visual signal that causes the pad 31 to appear to "snap" into place visually, whereas no such visual signal is produced by the orthogonal design of the pad 29. Preferably, the pad 31 is shaped to conform to the profile or outline of a statistically average maxillary right central of a population segment that is representative of the patient being treated with the appliance 33.

Figure 4A:
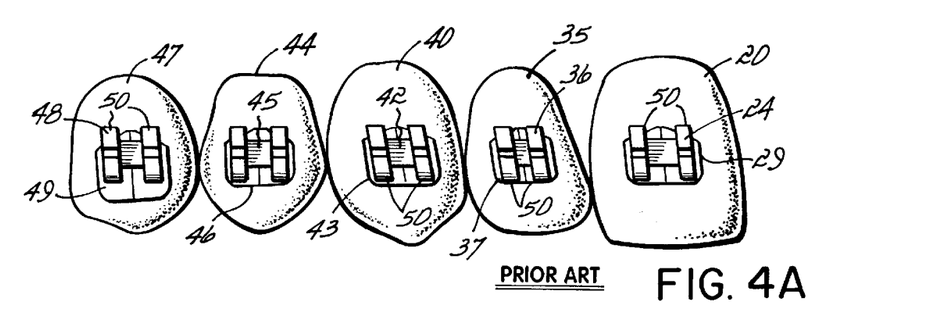
Figure 4B:
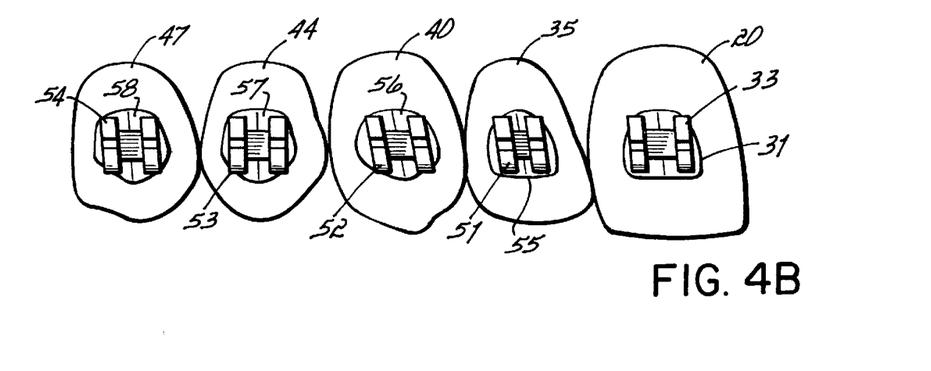
FIG. 4B is a similar diagram illustrating the placement on right maxillary teeth of tooth-shaped brackets according to principles of the present invention.

The pads of brackets of the present invention are preferably each designed for the different specific teeth of a patient. For each of the specific teeth of a patient (for example, for the maxillary right central 20, lateral 35, cuspid 40, first bicuspid 44 and second bicuspid 47), standard orthogonal brackets 24, 36, 42, 45 and 48 differ usually primarily in that the sides of their respective pads 29, 37, 43, 46 and 49 are parallel to the wings 50 of the brackets and correspond to the tip of the axis of the respective tooth, as illustrated in FIG. 4A. With the appliances of the present invention, brackets 33, and 51–54 are provided with pads 31, and 55–58 that are shaped to conform respectively to the outlines of the profiles of average teeth, 20, 35, 40, 44 and 47, as illustrated in FIG. 4B. Such pads, shaped so as to conform to the outlines of these teeth, are similarly illustrated. Such shapes additionally identify the brackets 33, 51–54 as being intended for the specific respective teeth 20, 35, 40, 44 and 47.

Figure 5A:
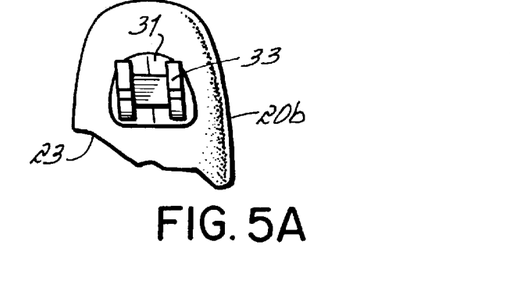
FIGS. 5A–5B and FIGS. 5C–5D are facial diagrams comparing the placement of the appliances of FIG. 3 and FIG. 2, respectively, in situations where the outline of the tooth on which it is placed is unclear.
Figure 5B:
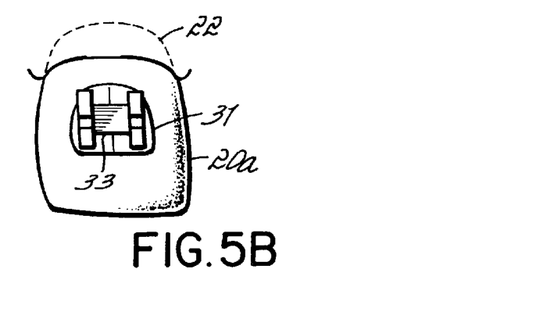
Figure 5C:
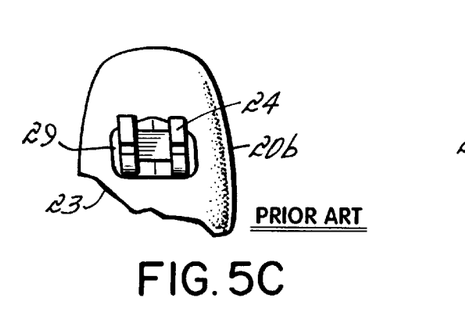
Figure 5D:
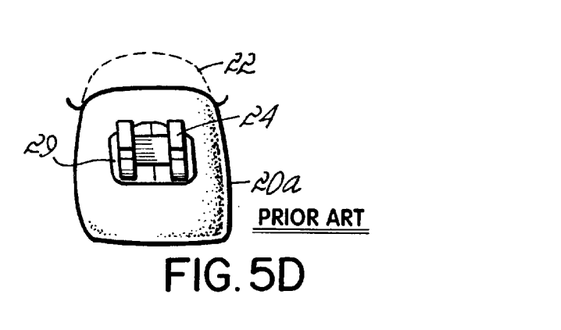

With pads shaped according to the present invention, the effects of the vagaries of chipped tooth incisal edges 23 and partial erupted portions 22 are also minimized, as illustrated in FIGS. 5A and 5B respectively, due to the increased perimeter of the pad 31 that is in register with the anatomy or outline of the tooth 20a or 20b, sending a stronger signal with respect to the totality of the remaining or apparent tooth. This is not the case with the standard bracket 21, as illustrated in FIGS. 5C and 5D.

Figure 6A:
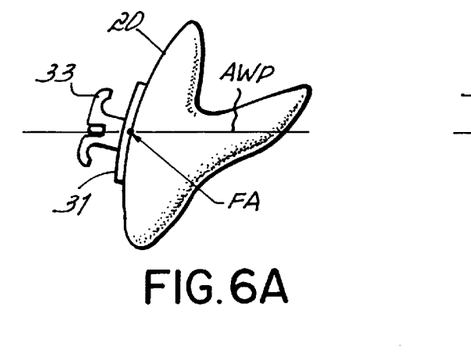
FIGS. 6A and 6B are mesial diagrams illustrating effective placement of the appliance of FIG. 3 for both standard and high torque prescriptions.
Figure 6B:
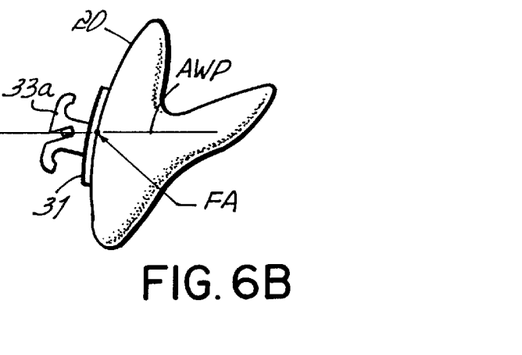
Figure 7:
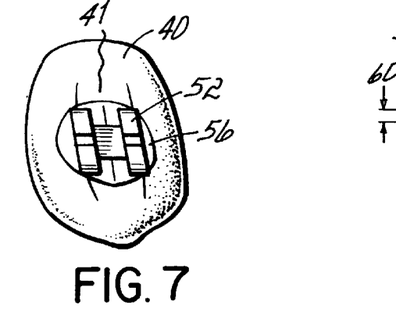
FIG. 7 is a facial diagram illustrating how off center placement of a bracket support can be achieved with the present invention.

With the tooth-shaped pads 31 and 55–58, calculated and precise location of the support portion of the brackets 33 and 51–55 upon the pads assures that the archwire plane AWP passes through the anatomical center of the pad irrespective of the particular appliance prescription chosen by the clinician. For example, as illustrated in FIGS. 6A and 6B respectively, for a bracket 33 having a standard prescription and for a bracket 33a having a high torque prescription, the true archwire plane AWP will tend to pass through the FA point with visual placement of the bracket 33 or 33a on the tooth 20. In addition, as illustrated in FIG. 7, when brackets having tooth-shaped pads are employed on teeth having a mid-developmental lobe 41 that is not in the middle of the facial view of the tooth, such as for the illustrated maxillary cuspid 40, the bracket 52 can accommodate the off-center lobe 41 by an adjusted placement of the bracket 52 on the pad 56, so that when the pad 56 is placed on the facial center of the tooth 40, the bracket will be mesiodistally displaced an appropriate amount. Compared with the bracket 42 having the standard orthogonal bracket pad 43 (FIG. 4A), the visual placement of the bracket 52 places the bracket 52 at the height of contour of the mid-developmental lobe 41 of the tooth 40, while the pad 56 will be placed by the clinician at the center in the facial view of the tooth 40. Compared with the bracket 42 having the standard orthogonal bracket pad 43 (FIG. 4A), the visual placement of the bracket 42 places the bracket 42 at the height of contour of the mid-developmental lobe 41 of the tooth 40, while the pad 43 will be placed by the clinician at the center in the facial view of the tooth 40.

Figure 8:
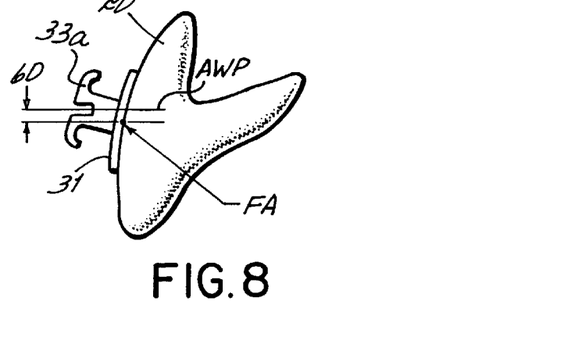
FIG. 8 is a mesial diagram illustrating an appliance positioned with a vertically offset the archwire plane in accordance with an embodiment of the present invention.

Also, the tooth-shaped bracket, such as the bracket 33a, can easily be designed so as to offset the archwire plane AWP vertically from the classic FA point on the tooth, for example, tooth 20, by a predetermined amount where the appliance is intended for such placement, as illustrated in FIG. 8. Such an offset position is likely to be accepted as a preferred modification to classic placement as the clinical bracket positioning art matures and more clinical evidence with respect to ideal placement is obtained. Such a bracket 33a is fixed so its support is at a vertical offset position on pad 31, which is still centered on the tooth 20 by visual placement, to give placement of archwire plane AWP by a predetermined distance 60 that is above or below FA point if desired.

The preferred method of the invention for determining the shapes of the bases of the appliances described above includes first producing outlines or profiles of each of the teeth of a patient, or of the teeth of a class of patients using statistical tooth shape data so that a standard outline for each tooth type, i.e., cuspid, central, etc., is produced. Preferably, each standard outline corresponds to a statistically average shape for all patients or statistical group of patients. From such outlines, a scaled down representation of each tooth shape is generated by reducing the tooth profiles in size to the desired sizes of the appliance bases. The size reduction may be uniform in all directions, but, preferably, different scales are used for different coordinates, such as by employing different vertical and horizontal dimension reductions. Most preferred is the use of a greater reduction of the vertical dimensions than of the horizontal dimensions, for example, by making the pads to a size of from 20 to 40% of the corresponding vertical dimensions of the tooth shape outlines and to from 40 to 60% of the corresponding horizontal dimensions of the tooth shape outlines.

Figure 9:
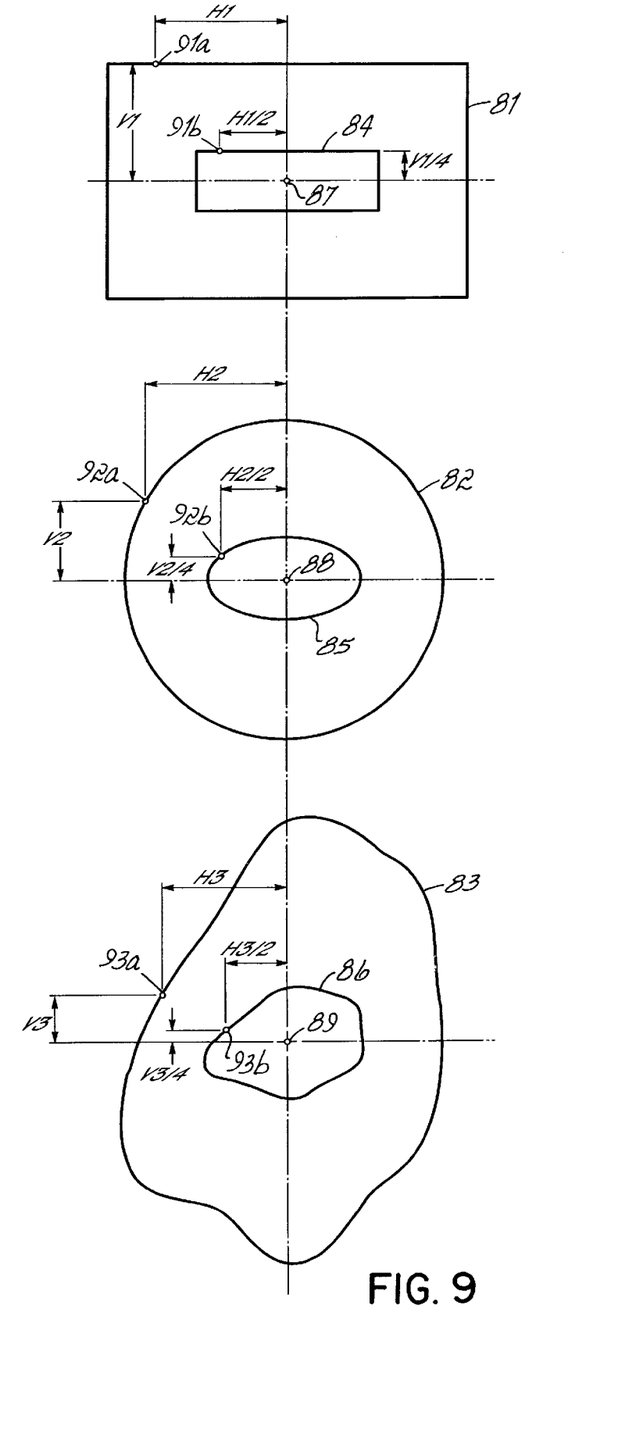
FIG. 9 is a series of diagrams illustrating one preferred manner of proportionally scaling the shape of the tooth profile to arrive at tooth-shaped brackets of the preferred embodiment of the present invention.

In FIG. 9 are illustrated a scaling of the outlines of a representative square profile 81, a circular profile 82 and an arbitrary shape 83 that can be regarded, for illustration purposes, as representative of the shape of a tooth. In each of the profiles 81–83 is respectively illustrated a correspondingly shaped form 84–86 which may be considered representative of the shape of an orthodontic appliance base or pad. The preferred method of proportionate size reduction used in each illustrated case scales the profiles by different amounts vertically and horizontally. The reduction illustrated uses a 25% scale factor in the vertical direction and a 50% scale factor in the horizontal direction. The centers of the profiles of each of the original shapes 81–83 are indicated at 87–89, respectively, on which the shapes of the pads 84–86 are respectively centered. Corresponding points on the corresponding shapes of the tooth outline and the pad outline, for example, points 91a and 91b, points 92a and 92b and points 93a and 93b, are respectively moved in the scaling step, vertically to one fourth of the original vertical distances $V_1, V_2, V_3$ from the horizontal centerlines, and horizontally one half of the horizontal distances $H_1, H_2, H_3$ from the vertical centerlines.

The appliances for which the present invention is most useful are the maxillary incisors, cuspids and bicuspids, on which the appliances are most often and most easily positioned visually.

Accordingly, those skilled in the art will appreciate that the application of the present invention is herein are varied, that the invention is described in preferred embodiments, and that additions and modifications can be made without departing from the principles of the invention.

Therefore, the following is claimed:

1. A method of providing an orthodontic appliance that is configured to be secured to a tooth that is unique one of the teeth of any one of a plurality of patients at a position on the tooth that is gingivally offset from the center of the tooth, the method comprising: providing an appliance comprising:

a bonding base adapted to be secured with adhesive to the facial side of said tooth of a patient, an archwire support extending rigidly from the base and having an archwire slot so positioned and oriented therein as to move said tooth to a predetermined treatment position and orientation when the base is centered on the facial side of said tooth, the base having a perimeter that is visually perceivable when placed against the facial side of the tooth and has a shape that is a scaled reduction of the characteristic outline of said unique one of the teeth when viewed from the facial side of said tooth whereby the base is centered and aligned on the facial side of said tooth when perimeter of the base is congruent with outline of the tooth, and the archwire support being located on the base gingivally offset from the center thereof so that, when the base is positioned on the facial side of said tooth with the base thereof is centered and angularly aligned on the facial side of said tooth, the slot is located in an archwire plane that is gingivally offset from the facial axis of the tooth; and placing the appliance on the facial side of the tooth, centering and angularly aligning the base thereon and adhesively bonding the centered and angularly aligned appliance to the tooth, whereby the slot of the appliance is located in an archwire plane that is gingivally offset from the facial axis of the tooth.

2. A method of providing an orthodontic appliance that is configured for mounting on a tooth that is specific one of the teeth of a patient and has a mid-developmental lobe mesiodistally offset from the facial view of the tooth, the method comprising: providing an appliance comprising:

an appliance mounting base, archwire support structure fixed to and extending from the base and having an archwire slot therein for supporting an archwire on a tooth in a predetermined position and an orientation defined in relation to the mid developmental lobe of the tooth, the appliance mounting base having a perimeter having a visually perceivable shape when placed against the facial side of the tooth, which shape is a scaled reduction of the characteristic outline of the typical profile of said specific one of the teeth, and the archwire support being mesiodistally offset from the center of the base such that, when the base is centered and oriented on the facial side of the tooth with the perimeter thereof centered and angularly aligned with the profile of said tooth, the archwire slot is located so as to support the archwire in the predetermined position and orientation in relation to the mid developmental lobe of the tooth; and placing the appliance on the facial side of the tooth, centering and angularly aligning the base thereon and adhesively bonding the centered and angularly aligned appliance to the tooth, whereby the slot archwire slot is located so as to support the archwire in the predetermined position and orientation in relation to the mid developmental lobe of the tooth.

3. A set of orthodontic appliances for treating the teeth of a patient, each of said teeth having a typical profile, when viewed from the facial side thereof, that is uniquely characteristic of the respective tooth and that visually distinguishes the respective tooth from each other tooth of the patient, the set comprising:

a plurality of orthodontic appliances, each uniquely provided for mounting on the facial side of a different one of the teeth of a patient, the set including at least eight different appliances including one for each of an upper right central, an upper left central, an upper right lateral, an upper left lateral, an upper right cuspid, an upper left cuspid, at least one upper right bicuspid and at least one upper left bicuspid;

each of said at least eight appliances including:

an appliance mounting base having a perimeter of a visually perceivable shape that is a scaled reduction of the typical profile of said respective one of the teeth and is characteristically different from the perimeters of the bases of each other appliance of the set and being sufficiently characteristic of the typical profile of said respective one of the teeth to identify the tooth of the patient for which it is uniquely provided;

archwire support structure fixed to and extending from the base and having an archwire slot therein for supporting an archwire on said respective one of the teeth in a predetermined relationship to the facial side of the tooth when said base is positioned on the facial side of said respective one of the teeth with the perimeter thereof centered and angularly aligned with the profile thereof so as to functionally cooperate with the other of said at least eight appliances to treat the teeth of the patient.

4. A method of manufacturing an orthodontic appliance having an appliance mounting base and an archwire slot formed in structure supported on the base so as to be positioned and oriented in a predetermined treatment position and orientation relative to the facial side of a given one of the teeth of a patient when the base is bonded in a unique proper position and orientation to the facial side of the tooth, the method comprising the steps of:

defining a characteristic tooth outline that is uniquely characteristic of the shape of the given one of the different teeth a typical one of a plurality of human patients;

forming an appliance base having a perimeter that is a scaled reduction of said defined characteristic tooth outline, the perimeter having a visually perceivable shape;

forming an archwire slot on the appliance in structure having a fixed relationship to the base so that, when the appliance is located on the facial side of the given one of the teeth of a patient with the perimeter of its base visually centered and angularly aligned relative to said outline, the archwire slot is in the predetermined treatment position and orientation relative to the facial side of the given one of the teeth; and packaging the appliance having the formed base and formed archwire slot for shipment to an office of an orthodontist for installation in the unique proper position and orientation on the given one of the teeth of a patient at which the archwire slot is in the predetermined treatment position and orientation relative to the facial side of the tooth.

5. A method of installing on a tooth of a patient an orthodontic appliance made according to the method of claim 4 further comprising the steps of:

removing the appliance from a package following shipment thereof to the office of an orthodontist; then, while viewing the facial side of the given one of the teeth of an individual patient, visually centering and angularly aligning the perimeter of the base relative to the outline of the facial side of said tooth to thereby position and angularly orient the archwire slot of the appliance in the predetermined treatment position and orientation relative to the base and bonding the base of the appliance to the facial side of the tooth of the patient to thereby provide the archwire slot installed in the predetermined treatment position and orientation relative to the facial side of said given tooth.

6. A set of orthodontic appliances for each of a plurality of different teeth of a patient, each manufactured according to the method of claim 4.

7. A method of placing an orthodontic appliance on a tooth of a patient, the tooth being anatomically identifiable as a selected one of thirty-two human tooth types, each tooth type having a characteristic outline and a facial axis where said tooth has an apparent profile partially reduced in area and interrupted along a segment thereof from the characteristic outline by one of partial eruption and tooth damage such that the apparent profile has an apparent center offset from the facial axis, the method comprising:

providing an orthodontic appliance comprising:

an appliance mounting base identifiably shaped to correspond to the characteristic outline for the selected one of thirty-two tooth types for visually indicating the facial axis of the tooth; and support structure fixed to and extending from the base, the support structure being located on the base so that, when the base is positioned on the facial side of the tooth of the patient for bonding thereto with the perimeter thereof centered and angularly aligned at a predetermined treatment position and orientation relative to the facial axis of the tooth, notwithstanding the offset of the apparent center of the apparent profile; and positioning the appliance on said tooth by visually centering and aligning the base with the outline of the tooth; and bonding the base of the positioned appliance to said tooth.

8. The method of claim 7, wherein the support structure of the appliance has an archwire slot therein for supporting an archwire in an archwire plane, which plane, when the appliance is bonded to the facial side of said tooth in the predetermined treatment position and orientation, intersects the surface of the facial side of the tooth at a location vertically offset from the facial axis of the tooth.

9. The method of claim 8, wherein said tooth has a mid-developmental lobe that is not mesiodistally centered on the facial view of the tooth, the support structure of the appliance is mesiodistally offset from the center of the base so that the archwire slot thereof is located to support the archwire on the tooth in said mesiodistal relationship to the mid developmental lobe of the tooth.

10. The method of claim 8 wherein:

the support structure of the appliance is located on the base gingivally offset from the center thereof so that, when the base is positioned on the facial side of said tooth for bonding thereto with the perimeter thereof centered and angularly aligned with the profile of the facial side of the tooth, the slot thereof is located to support an archwire in an archwire plane that is gingivally offset from the facial axis of the tooth.

11. A method of placing a set of orthodontic appliances on the teeth of a patient where at least one of the teeth of the patient to be treated has an apparent profile partially reduced in area and interrupted along a segment thereof from the characteristic outline by one of partial eruption and tooth damage such that the apparent profile has an apparent center offset from the facial axis, the method comprising:

providing a plurality of orthodontic appliances, each for mounting on the facial sides of a different one of the teeth of a patient to be treated, each of thirty-two human tooth types having a characteristic outline a facial axis, the set including at least eight different appliances including one for each tooth type of an upper right central, an upper left central, an upper right lateral, an upper left lateral, an upper right cuspid, an upper left cuspid, at least one upper light bicuspid and at least one upper left bicuspid; each of said at least eight appliances of the set including:

an appliance mounting base identifiably shaped to correspond to the characteristic outline for the selected one of thirty-two tooth types for visually indicating the facial axis of the tooth, and a support structure fixed to and extending from the base, the support structure being located on the base so that, when the base is positioned on the facial side of the tooth of the patient for bonding thereto with the perimeter thereof centered and angularly aligned at a predetermined treatment position relative to the facial axis of the tooth, notwithstanding any offset of the apparent center of the apparent profile; and positioning each appliance on each of said teeth by visually centering and aligning the base with the outline of the respective tooth; and bonding the bases of the positioned appliances to each of the respective teeth.

12. The method of claim 11, wherein the support structure of each of the orthodontic appliances of the plurality has an archwire slot therein for supporting an archwire in an archwire plane, which plane, when each of the plurality of appliances are bonded to the facial side of each respective tooth in a predetermined treatment position and orientation, intersects the surface of the facial side of each respective tooth so as to functionally cooperate with appliances of the set on other teeth of the patient without further adjustment of the position and orientation of the appliance on the tooth and without bending of the archwire.

13. A method of providing an orthodontic appliance for mounting on a tooth of a patient, said tooth anatomically identifiable as a selected one of thirty-two human tooth types, each tooth type having a characteristic outline and a facial axis, said tooth having an apparent profile partially reduced in area and interrupted along a segment thereof from the characteristic outline by one of partial eruption and tooth damage such that the apparent profile has an apparent center offset from the facial axis, the method comprising:

manufacturing said appliance by:

forming an appliance mounting base to identifiably correspond in shape to the characteristic outline for the selected one of thirty-two tooth types for visually indicating the facial axis of the tooth, and extendingly fixing a support structure to the base, the support structure being located on the base so that, when the base is positioned and aligned on the facial side of said tooth at a predetermined treatment position relative to the facial axis of the tooth, notwithstanding the offset of the apparent center of the apparent profile from the facial axis;

placing said appliance in a package and shipping said appliance to the office of an orthodontist for placement on said tooth by visually centering and aligning said appliance with the outline of the tooth.

14. A method of installing on a tooth of a patient an orthodontic appliance made according to the method of claim 13, the method further comprising:

removing the appliance from a package following shipment thereof to the office of an orthodontist;

visualizing the facial axis of said tooth by referencing the base and viewing the facial side of said tooth, notwithstanding the apparent center offset from the facial axis;

visually positioning and angularly aligning the perimeter of the base relative to the visualized facial axis on the facial side of said tooth to thereby position and orient the support structure of the appliance in the predetermined treatment position and orientation; and while so positioned and aligned, bonding the base of the appliance to the facial side of said tooth.

15. An orthodontic appliance adapted to be mounted on a tooth of a patient by being visually centered and aligned with the outline of the tooth, said appliance being manufactured and packaged according to the method of claim 13.

16. A set of orthodontic appliances for each adapted to be mounted on each of a plurality of different teeth of a patient by being visually centered and aligned with the outline of the respective tooth, each of said appliances being manufactured and packaged according to the method of claim 13.

17. A method of providing an orthodontic bracket on the facial side of the crown of a specific tooth of a patient, said specific tooth being one of either an upper or a lower, either right or left, central, lateral, cuspid, first bicuspid or second bicuspid, the method comprising:

manufacturing an orthodontic bracket having:

a base having a perimeter that includes mesial, distal, occlusal and gingival edges that have the same orientation relative to each other as corresponding edges of a statistically average profile of the crown of said specific tooth of a representative plurality of human patients, the base having a width between its mesial and distal edges and a height between its occlusal and gingival edges that less than the respective width and height between the corresponding edges of said statistically average profile of said specific tooth, with the ratio of the height to the width of the base being less than the ratio of the height to the width of said statistically average profile, the gingival edge of the base being curved and generally parallel to the gingival edge of said statistically average profile of a fully erupted crown of said specific tooth, and         an archwire support fixed to the base having an archwire slot therein that is located so as to be in a predetermined treatment position and orientation relative to the crown of the specific tooth of the patient when the base is congruently centered and oriented on said crown relative to its respective mesial, distal, occlusal and gingival edges; and     while viewing the facial side of said specific tooth of the patient, placing the base of the bracket against the specific tooth of the patient and visually adjusting the position and angular alignment of the perimeter of the base relative to the profile of the facial side the crown of said specific tooth until the perimeter of the base is substantially visually congruent therewith, then adhesively bonding the base to the crown, thereby locating the slot in the predetermined treatment position and orientation on the specific tooth.

18. A set of orthodontic appliances, each differently configured to be secured to a tooth that is a different unique one of the teeth of any one of a plurality of persons and each configured to function, when interconnected with an archwire to move the teeth of a patient to respective predetermined treatment positions and orientations, each appliance comprising:

a bonding base adapted to be secured with adhesive to the facial side of the respective tooth;

a archwire support extending rigidly from the base and having an archwire slot so positioned and oriented therein as to move said respective tooth to a respective one of the predetermined treatment positions and orientations when the base is centered and aligned on the facial side of said tooth; and     the base having a perimeter that is visually perceivable when placed against the facial side of said tooth and has a shape that differs from the shapes of the bases of each of the other appliances of the set and is a scaled reduction of the characteristic outline of the corresponding unique one of the teeth of the plurality of persons when viewed from the facial side thereof, the base being centered and aligned on the facial side of said tooth when the perimeter of the base is congruent with outline of the tooth.

19. A method of placing on a tooth that is unique one of the teeth of any one of a plurality of patients an orthodontic appliance that is configured to be secured to said tooth, the method comprising: providing an appliance having:

a bonding base adapted to be secured with adhesive to the facial side of said tooth of a patient,     a archwire support extending rigidly from the base and having an archwire slot so positioned and oriented therein as to move said tooth to a predetermined treatment position and orientation when the base is centered on the facial side of said tooth, and     the base having a perimeter that is visually perceivable when placed against the facial side of the tooth and has a shape that is a scaled reduction of the characteristic outline of said unique one of the teeth when viewed from the facial side of said tooth, whereby the base is centered and aligned on the facial side of said tooth when perimeter of the base is congruent with outline of the tooth;

placing the base of the appliance on the facial side of said tooth; and     visually adjusting the position and orientation of the appliance on said tooth until perimeter of the base is congruent with the outline of said tooth; and     adhesively fixing the appliance to the facial side of said tooth in the adjusted position and orientation.

20. A method of placing on a tooth that is unique one of the teeth of any one of a plurality of patients an orthodontic appliance that is configured to be secured to said tooth, said tooth having a profile, when viewed from the facial side of the tooth, that includes mesial, distal, occlusal and gingival edges, the method comprising: providing an appliance having:

a bonding base adapted to be secured with adhesive to the facial side of said tooth of a patient,     a archwire support extending rigidly from the base and having an archwire slot so positioned and oriented therein as to move said tooth to a predetermined treatment position and orientation when the base is centered on the facial side of said tooth, and     the base having a perimeter that is visually perceivable when placed against the facial side of the tooth and has a shape that is a smaller than the profile of the tooth and includes mesial, distal, occlusal and gingival edges, whereby the base is centered and aligned on the facial side of said tooth when perimeter of the base is generally centered on said tooth with the mesial, distal, occlusal and gingival edges thereof oriented generally parallel to the respective mesial, distal, occlusal and gingival edges of said tooth;

placing the base of the appliance on the facial side of said tooth;

visually adjusting the position and orientation of the appliance on said tooth until perimeter of the base is congruent with the outline of said tooth; and     adhesively fixing the appliance to the facial side of said tooth in the adjusted position and orientation.

\* \* \* \* \*

UNITED STATES PATENT AND TRADEMARK OFFICE
CERTIFICATE OF CORRECTION

PATENT NO. : 6,358,044 B1
DATED : March 19, 2002
INVENTOR(S) : Craig A. Andreiko It is certified that error appears in the above-identified patent and that said Letters Patent is hereby corrected as shown below:

Column 4,
Lines 1-2, reads "… may be defined in relation to the a point…" and should read
-- … may be defined in relation to a point… --.
Line 30, reads "… of the shapes from the that of the…" and should read -- … of the shapes from that of the… --.

Column 5,
Line 56, reads "with a vertically offset the archwire plane in. ….." and should read
-- with a vertically offset archwire plane in. .. --.

Column 7,
Line 37, reads "…mid-developmental lobe 41 of the tooth 40, while the pad 43…" and should read -- …mid-development al lobe 41 of the tooth 40, while the pad 56… --.

Column 8,
Line 34, reads "… application of the present invention is herein are varied,…" and should read -- … applications of the present invention herein are varied,… --.
Line 62, reads "… with the base thereof is centered and angularly aligned on the facial…" and should read -- … with the base thereof centered and angularly aligned on the facial… --.

Column 9,
Line 33, reads "… aligned appliance to the tooth, whereby the slot archwire slot is located so as to support the…" and should read -- … aligned appliance to the tooth, whereby the slot archwire is located so as to support the… --.

Column 10,
Lines 13-14, reads "… shape of the given one of the different teeth a typical one of a plurality of human patients;" and should read -- …shape of the given one of the different teeth of a typical one of a plurality of human patients; --.

Column 11,
Line 53, reads "…upper left cuspid, at least one upper light bicuspid and…" and should read -- …upper left cuspid, at least one upper right bicuspid and… --.

UNITED STATES PATENT AND TRADEMARK OFFICE
CERTIFICATE OF CORRECTION

PATENT NO.   : 6,358,044 B1
DATED        : March 19, 2002
INVENTOR(S)  : Craig A. Andreiko It is certified that error appears in the above-identified patent and that said Letters Patent is hereby corrected as shown below:

<u>Column 13,</u>
Line 12, reads "...occlusal and gingival edges that less than the respective..." and should read -- ...occlusal and gingival edges that is less than the respective... --.
Line 33, reads "...base relative to the profile of the facial side the crown..." and should read -- ..base relative to the profile of the facial side of the crown ... --.

<u>Column 14,</u>
Line 46, reads "...a shape that is a smaller than the profile of the tooth and..." and should read -- ...a shape that is smaller than the profile of the tooth and... --.

Signed and Sealed this

Fourth Day of March, 2003

JAMES E. ROGAN
*Director of the United States Patent and Trademark Office*